United States Patent [19]

Tang et al.

[11] Patent Number: 5,214,194
[45] Date of Patent: May 25, 1993

[54] COUPLER INTERMEDIATES AND THEIR FORMATION

[75] Inventors: Ping-Wah Tang, Rochester, N.Y.; Jeffrey R. Neff, Kingsport, Tenn.; Frank T. Melia; Donald J. Schuster, both of Rochester, N.Y.

[73] Assignee: Eastman Kodak Company, Rochester, N.Y.

[21] Appl. No.: 764,598

[22] Filed: Sep. 24, 1991

[51] Int. Cl.⁵ .............................. C07C 67/14
[52] U.S. Cl. ...................... 560/142; 564/223; 564/443
[58] Field of Search .......................... 560/142

[56] References Cited

U.S. PATENT DOCUMENTS

| 4,127,671 | 11/1978 | Cognacq | 560/142 X |
| 4,568,763 | 2/1986 | Davenport et al. | 560/142 |
| 4,584,318 | 4/1986 | Peake et al. | 560/142 X |
| 4,665,216 | 5/1987 | Horlenko et al. | 560/142 |

OTHER PUBLICATIONS

Liotta et al., *J. Org. Chem.* 39, 1976, 2718–2722 (1974).
Armen et al., *Tetrahedron Letters*, 43, 4197 to 4200, (1979).
Liotta et al., *J. Org. Chem.* 39, 3445–3446, (1973).
Stahl et al., *J. Org. Chem.* 45, 1197–1202, (1980).
Heistand II et al., *J. Org. Chem.* 43, 3613–3615, (1978).

*Primary Examiner*—José G. Dees
*Assistant Examiner*—Vera C. Clarke
*Attorney, Agent, or Firm*—Arthur E. Kluegel

[57] ABSTRACT

A process for the preparation of 5-substituted 2-aminophenols via nitrones, comprises two reactions. First, a nitrone is reacted with a trihaloacetyl halide to regiospecifically convert the nitrone to a 5-substituted-2-aminophenol derivative (I). Subsequently, the derivative is hydrolyzed to form the 5-substituted-2-aminophenol. The product is useful as a chemical intermediate, e.g. for the preparation of couplers used in photographic chemistry.

4 Claims, 1 Drawing Sheet

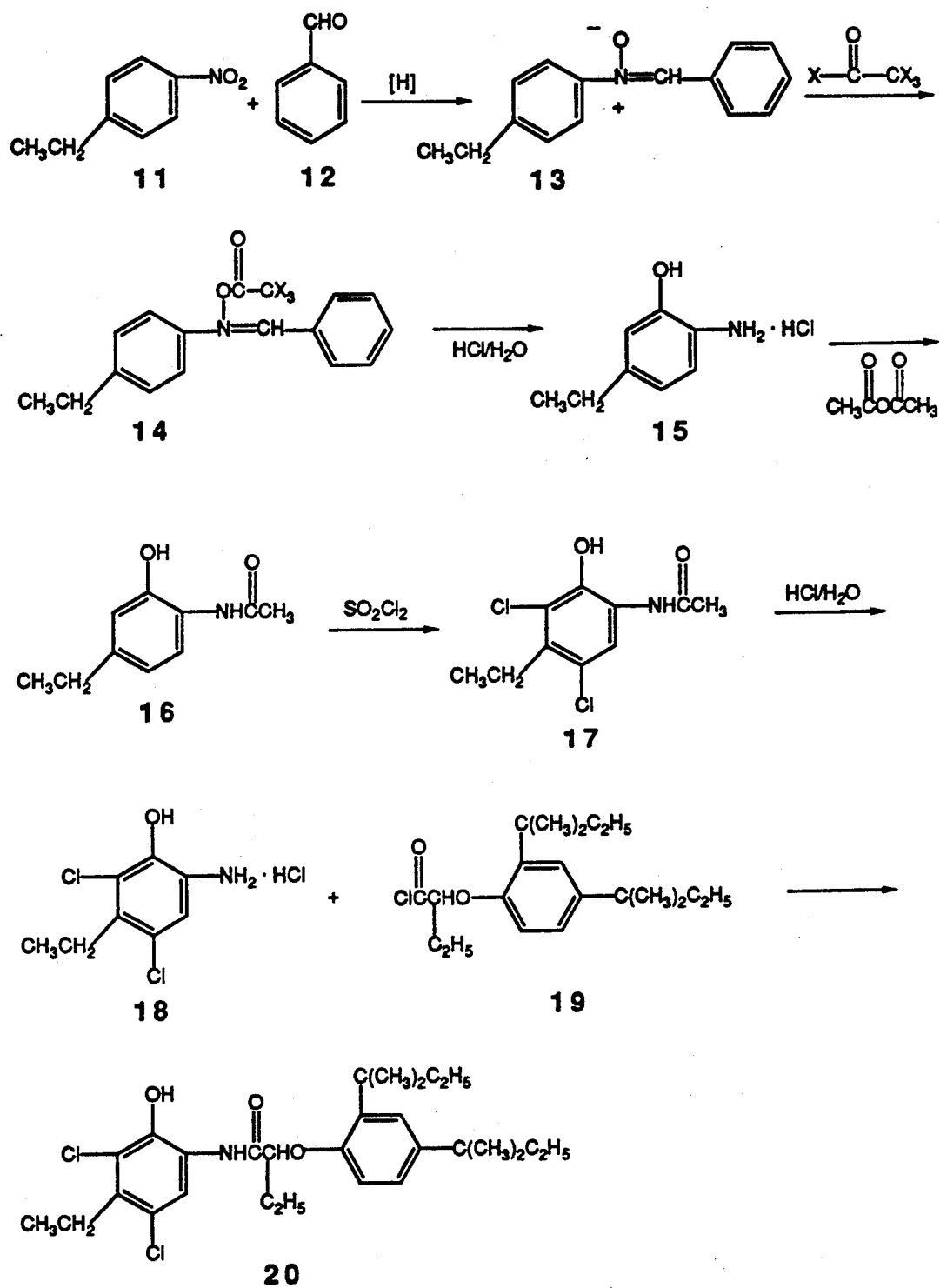

COUPLER INTERMEDIATES AND THEIR FORMATION

FIELD OF THE INVENTION

This invention relates to the preparation of aminophenols having substituents para to the amino function. More particularly, this invention relates to preparation of 2-aminophenols which have a substituent at the position para to the amino group. These materials are useful as chemical intermediates, e.g., for the preparation of color photographic dye formers.

A process of this invention comprises two steps: (a) reacting a nitrone and a trihaloacetyl halide, and (b) subsequently hydrolyzing the intermediate thereby produced. The intermediate, which need not be isolated, is a compound of this invention. The process steps provided by this invention are surprisingly clean; in other words, they form little or no unwanted by-products.

BACKGROUND OF THE INVENTION

It is known in the art that both the amino and the hydroxy group are ortho and para directing. It is also known that when both groups are on an aryl ring, substitution reactions generally lead to a mixture of ortho and para isomers, and frequently to polysubstituted products. Needless to say, the formation and separation of isomeric mixtures greatly reduces product yields. For example, the synthesis of 2-amino-5-methylphenol involves only two reaction steps: (1) nitration of 3-methylphenol (meta-cresol) and (2) reduction of the nitro intermediate. However, the overall yield is very poor (less than 30%), due to the formation of other nitro isomers and the need to separate this mixture by steam distillation.

It is known in the art that 5-substituted-2-aminophenols are useful intermediates, for example, in the photographic industry. Unfortunately, this type of compound is generally hard to make in pure form and in good yield, for the reasons stated above.

RELATED ART

The following references disclose that 2-amino-5-methylphenol is produced in poor yield when meta-cresol is nitrated and then reduced: R. C. Huston et al, J.Am.Chem.Soc. 55, 3879 (1933); W. Staedal et al, Ann.Chem. 259, 210 (1890); J. Arient, Collect Czech. Chem. Comm. 45, 3164 (1980).

In addition, U.S. Pat. No. 4,490,812 issued to co-workers of the Applicants, sets forth an elegant synthesis of 5-substituted aminophenols from (a) aminophenols having hydrogen or a coupling off group in a position para to the phenolic OH, (b) an unhindered non-enolizable aldehyde, and (c) a thiol or sulfinic acid. That method involves use of a reactant having an —OH and an NH$_2$ group. In contrast, this invention uses different reactants and involves an elegant synthesis of an —OH group ortho to an amino function. Thus, the process of this invention provides a means for forming 2-aminophenols when the starting materials for processes described in U.S. Pat. No. 4,940,812, are not readily available.

Stated another way, this invention provides an elegant means for putting a hydroxy group on an aromatic ring at a desired location. The reaction conditions for this synthesis are mild, and easily carried out. Little or no undesired by-product is formed, in contrast to some known synthetic routes discussed above.

It is not known in the art that trihaloacetyl halides will react with nitrones to form a compound of Formula (I), below. Although oxalyl chloride is known to give a compound analogous to Formula (I) when reacted with a nitrone, Liotta et al, J. Org. Chem. 39, 1976 (1974), other active halogen compounds do not. For example, it is known in the literature that phosgene and thionyl chlorides react to form a chloro derivative of a nitrone; Liotta et al, J. Org. Chem. 39, 2718 (1974). In addition, work by prior workers has demonstrated that benzoyl chloride did not react with a nitrone to form the desired product; Stahl et al, J. Org. Chem. 45, 1197 (1980).

BRIEF DESCRIPTION OF THE DRAWING

The drawing illustrates (a) the preparation of starting materials for this invention, (b) the processes and (c) compounds of the invention, and (d) use of this invention for the formation of a coupler, i.e. a color photographic dye former.

Referring to the drawing, reaction of compounds 11 and 12 (catalytic or chemical reduction) yields compound 13, a nitrone which is useful as a starting material for this invention. Reaction of compound 13 with a trihaloacetyl halide yields compound 14, a compound of this invention. The hydrolysis of Compound 14 is a second step of an embodiment of this invention. Compound 15 is a salt of a 2-aminophenol. As shown in the drawing, it is prepared by the process steps of this invention. The aminophenol can be freed from its salt if desired, but for some purposes it is not necessary to do so. Subsequent transformations in the drawings now illustrated how such an aminophenol salt can be transformed into a coupler for use in color photographic material. Coupler 20 forms a cyan dye, when reacted with an amine developer, such as those commonly employed in photoprocessing in accordance with development processes known in the art.

Reactions illustrated in the FIGURE which are subsequent to formation of Compound 15 show a preferred use of this invention, but are not part of this invention. The reactions can be conducted by a practitioner having ordinary skill in the art.

SUMMARY OF THE INVENTION

This invention provides a simple and efficient one-pot reaction for forming 5-substituted-2-aminophenols useful as intermediates in the photographic arts. The process provides a means for introducing a hydroxy group onto an aromatic ring regiospecifically, i.e. at a position ortho to a nitrogen-containing functional group. Key intermediates are obtained in high yield, with little or no contamination with unwanted by-products. The intermediates are compounds of this invention. The nitrones used as starting materials are readily formed from aldehydes and nitro-substituted aromatics, e.g. para-substituted nitrobenzenes.

Since the invention provides easy entry to a wide variety of 5-substituted-2-aminophenols useful for forming cyan couplers, the invention is readily adaptable by industry, and considered to be a significant advance in the art.

DESCRIPTION OF PREFERRED EMBODIMENTS

In one embodiment, this invention provides: as a composition of matter, a compound having the formula

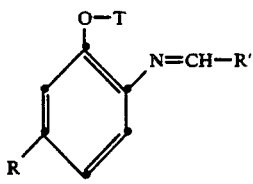

wherein T has the formula:

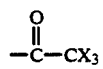

wherein each X is independently selected from iodine, chlorine and bromine, R is an alkyl group of 1 to about 10 carbon atoms or a coupling off group, and R' is an alkyl or aryl group having up to about 10 carbon atoms.

In another embodiment, this invention provides a process for preparing compounds having above formula (I), said process comprising reacting a trihaloacetyl halide with a nitrone having the formula

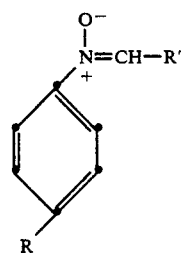

wherein R and R' are as defined above.

In a third embodiment, this invention provides a process for forming a 5-substituted 2-aminophenol, said process comprising hydrolyzing a compound having formula (I).

In still another embodiment, this invention provides a process for preparing 5-substituted 2-aminophenols which comprises (a) reacting a nitrone having formula (II) with a trihaloacetyl halide, to form a compound of formula (I), and (b) subsequently hydrolyzing that compound.

As indicated above, this invention employs nitrones as starting materials. Preferred nitrones are made from aldehydes. The invention is not limited by the method of forming the nitrone employed. Any method known in the art which successfully makes nitrones of the type described herein can be used. Nitrones can be made from oximes, of March, J., *Advanced Organic Chemistry*, Wiley-Interscience, New York, N.Y. 3rd Edition, page 359.

A preferred method for formation of nitrones is the reaction of a para-substituted aromatic nitro compound with an aldehyde under reducing conditions. This synthesis is described in Mylroie et al., Chapter 12 in J. R. Kosak *Catalyes of Organic Reactions*, Marcel Dekker, Inc., New York, N.Y. For small scale work, an aromatic aldehyde such as benzaldehyde or p-tolualdehyde is conveniently employed. For larger scale work where cost is more of a factor, one may wish to use an aliphatic aldehyde. Any aldehyde which is readily obtainable and sufficiently reactive can be used. Thus, aliphatic aldehydes, particularly alkyl aldehydes and aromatic aldehydes having up to about 10 carbon atoms are preferred. In fact, the part of the nitrone molecule which is obtained from the aldehyde is reacted off, i.e. removed, when the method embodiment(s) of this invention are used to form a 5-substituted-2-aminophenol.

The nitrone has a substituent in the position para to the nitrone moiety,

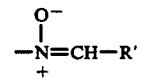

That substituent may be relatively inert one such as an alkyl group having up to about 10 carbon atoms, or a coupling off group.

Since the process steps of this invention are especially efficacious for preparing 5-substituted-2-aminophenols useful for preparing photographic chemicals, one embodiment of this invention comprises preparation of compounds in which R in formula (I) is a coupling off group.

Coupling-off groups, defined by Z herein, are well known to those skilled in the photographic art. Such groups can determine the equivalency of the coupler, can modify the reactivity of the coupler, or can advantageously affect the layer in which the coupler is coated or other layers in the element by performing, after release from the coupler, such functions as development inhibition, bleach acceleration, color correction, development acceleration, and the like. Representative classes of coupling-off groups include halogen, particularly chlorine or fluorine, alkoxy, aryloxy, heterocyclyloxy, sulfonyloxy, acyloxy, carbonamido, imido, heterocyclic, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212; and 4,134,766; and in U.K. patents and published application nos. 1,466,728; 1,531,927; 1,533,039; 2,006,755A; and 2,017,704A, the disclosures of which are incorporated herein by reference.

Examples of specific coupling-off groups are as follows:

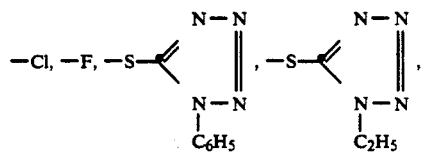

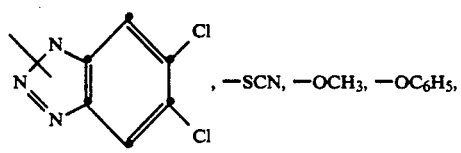

—OCH₂CONHCH₂CH₂OH, —OCH₂CONHCH₂CH₂OCH₃,

—OCH₂CONHCH₂CH₂OCOCH₃,

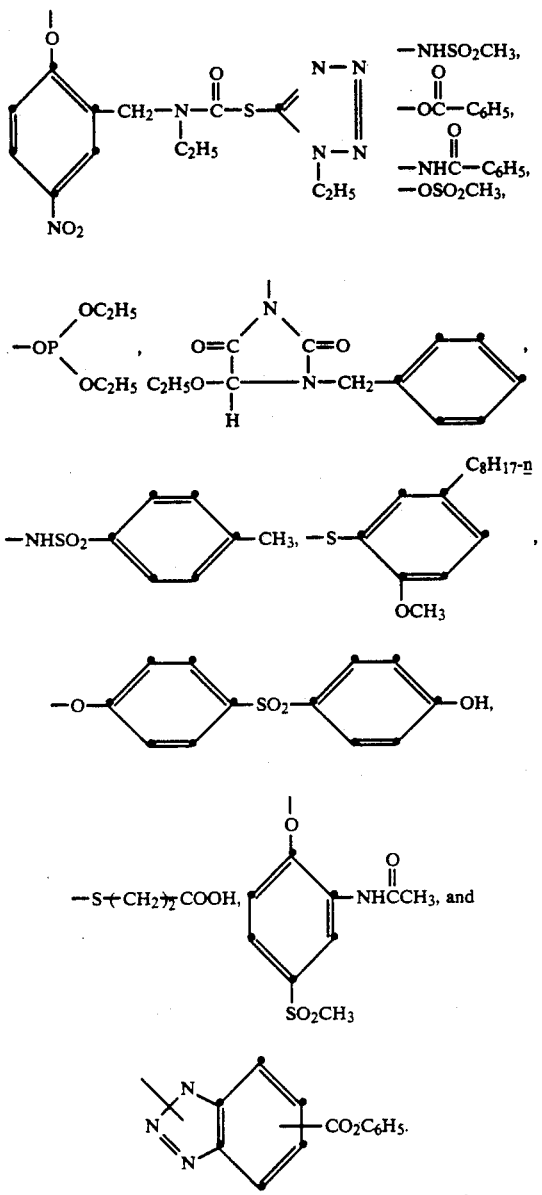

The coupling-off group as described can contain a water-solubilizing group, such as a carboxy group. The total hydrophilicity of the coupler and the dye formed from the coupler should not be high enough to cause the coupler and the dye formed to be mobile in the photographic element.

The reactants may have "inert" substituents on the ring. Typical "inert" substituents are alkyl, alkoxy, halogen, and the like. Such substituents are exemplified by —$CH_3$, —$C_{10}H_{21}$, —$C_{14}H_{29}$, $OCH_3$, —$OC_{10}H_{21}$ —$OC_{14}H_{29}$, —Cl, —F, and the like.

As illustrated by the figure in the drawing, the processes of this invention employ a nitrone as a starting material. The nitrone has a substituent para to the nitrone functionality. Preferably, the two positions ortho to the nitrone moiety are unsubstituted; in other words, the carbon atom on the benzene nucleus (to which the nitrogen atom in the nitrogen oxide functionality is attached) are bonded to hydrogens. The inventors contemplate a reaction in which one of the aforesaid ortho positions is substituted with something other than hydrogen. However, compounds have no ortho substituent are preferred.

Nitrones, such as discussed above, are reacted with a type of acyl halide to form compounds of this invention. Thus, the nitrones are reacted with an a trihaloacetyl halide to from the compounds of this invention. The halogens may be iodine, bromine, chlorine, or mixtures thereof; more preferably bromine or chlorine. Preferably all of the halo substituents are the same, and most preferably they are chlorine. Hence, trichloracetyl chloride is a preferred reactant for preparing compounds of this invention.

The nitrone function and the halide in the acyl halide reactant combine in a molar ratio of one to one. However, it is not necessary that the reactants be admitted to the reaction zone in that mole ratio. Thus, an excess of either reactant may be used to help drive the reaction toward completion. In a preferred embodiment, a slight excess of the halide reactant (trihaloacetyl halide) is used. There is no real upper limit on the amount of excess, this being defined by such secondary characteristics as the size of the reaction vessel, ease of separation of products, process economics, and the like. In general, one employs from about 1.01 to about 10 moles of one reactant per each one mole portion of the other. Preferably, the mole excess is from about 0.1 to 1.0 mole per mole of the other reactant. Thus, in a preferred embodiment, one employs 1.1 to 2.0 moles of acyl halide per each mole portion of nitrone.

In the processes of this invention, the reactants are combined under reaction conditions. Thus, in the process step in which a compound of Formula (I) is prepared, the process is conducted under substantially anhydrous conditions, in order to avoid extraneous side reaction(s) that diminish the yield of desired product. In general, the water content should be below about 0.1 weight percent. In order to achieve such substantially anhydrous conditions, one may add previously dried ingredients to the reaction zone. Alternatively, or as an added precaution, one may by some suitable means, remove water which is present. For example, one can remove water by forming a distillable azeotrope with toluene. The latter expedient is especially useful when the nitrone is reacted in the reaction mixture in which it is formed (from an aldehyde and a para-substituted nitrobenzene).

In both steps provided by this invention for the preparation of a 2-amino-5-substituted phenol, a reaction medium can be used to facilitate contacting the reactants. The nature of the solvent(s) employed for these steps is not critical, and a wide variety of solvents can be used. Generally, one employs a solvent having suitable solvent power for the reactants that are being employed, and which is inert or relatively inert under the reaction conditions used. Thus, one selectes a solvent in which the reactants are sufficiently soluble, and which is relatively inactive toward the reactants and product, and which does not decompose under the reaction conditions employed. For the purposes of this invention, such solvents are termed "inert solvents".

For the reaction of a nitrone with a trihaloacetyl halide, a halogenated alkane solvent or cyclic ether such as THF (tetrahydrofuran) are preferentially employed. Of this type of solvent, methylene chloride is preferred. Other halogenated lower alkanes can be used. If this type of reaction medium selected, due care should be employed so that such materials are maintained appropriately from a toxicological and environmental viewpoint.

For the reaction of a compound of Formula (I) with water, the hydrolysis step, a polar solvent is conveniently employed. One may use a carboxylic acid, such as acetic acid or a homolog thereof having up to about four carbons, or an alcohol such as ethanol, methanol or the like, e.g., a lower alcohol having up to about four carbon atoms.

For either step, there is nothing critical about the amount of solvent employed, and the amount selected is generally within the skill of the art. In general, one employs enough solvent to facilitate contacting the reactants, but not so much as to make the process unduly expensive by raising materials costs, or by complicating recovery of desired products or solvent for reuse. As can be seen from the above, there is no real upper limitation on the amount of solvent that can be employed. Consequently, any practical limitation on the upper limit is governed by the size of the reaction vessel, process economics, or such other secondary consideration.

The process steps of this invention can be conducted at any convenient pressure. Ambient pressure is preferred, but an elevated pressure can be used, when for example such an expedient assists keeping a comparatively volatile material in the reaction zone. Generally, reduced pressures offer no real advantage and therefore they are not recommended. Thus as can be seen, the reaction pressure is not a critical variable, and its selection is well within the ordinary skill of the art.

The reaction temperature is selected so that a reasonable rate of reaction is achieved without an untoward amount of decomposition or undesired side reaction. When the nitrone is reacted with the acyl halide, the temperature is generally between about −20° C. and about 50° C. When the product of formula (I) is hydrolyzed, the reaction temperature is generally between about generally between about 0° C. and 50° C. Ambient temperature is convenient for both steps. Temperatures somewhat outside the ranges given above can be employed, if desired. Generally, the temperature does not exceed the normal boiling point of the solvent or other low boiling species which is preferably kept in the reaction zone.

The reaction time is not a truly independent variable and is dependent in part at least on such considerations as the inherent reactivity of the reactants employed, the reaction temperature, etc. Generally speaking, the higher the temperature, the shorter the reaction time. In general, the reaction to prepare a compound of Formula (I) is usually essentially complete in from about 0.5 to about 60 minutes, and the reaction in which such a compound is hydrolyzed can be complete in about the same time range when the temperatures given above are employed. Longer and shorter reaction times can be used if desired.

The following examples serve to illustrate the invention and not to limit it.

EXAMPLE 1

4-Ethyl-N-(4-methylbenzylidene)benzeneamine N-oxide

In a 5-L 4-necked round bottom flask equipped with a stirrer, thermometer, dropping funnel and ice-acetone bath was placed 2800 mL of methanol, 300 mL of distilled water, 400 g (2.64 moles, 1.0 equiv.) of 4-ethyl-1-nitrobenzene (11), 349.7 g (2.9 moles, 1.1 equiv.) of p-tolualdehyde, and 367.5 g (5.62 moles, 2.13 equiv.) of zinc powder. The reaction mixture was cooled to 0° C., then with vigorous stirring the dropwise addition of 792.0 g (13.2 moles, 5.0 equiv.) of acetic acid was started. There was a 3-5 minute induction period before the exotherm began. When the acetic acid addition was complete, the reaction mixture was stirred for 1 hour at 10° C. The reaction mixture changes from gray opaque to greenish white, which signifies reaction completion. The reaction mixture was checked for reaction completion by TLC (1 BuOAc, 2 PhCH$_3$, 4 CHCl$_3$) eluted on silica-gel and viewed under short-wave UV light. After the 1 hour reaction period, 500 mL of dichloromethane was added to solubilize any undissolved product. The zinc acetate salts were filtered off ($\simeq$1 kg) and washed with 200-300 mL of dichloromethane. (Salts may also be slurried in dichloromethane to remove any remaining product.) The filtrates were stripped to a mush under aspirator vacuum to a pot temperature of 57° C. The green mush was cooled to 25° C. and 1000 ml of dichloromethane and 1000 mL of distilled water were added to the flask. The mixture was stirred vigorously to dissolve all product and salts, then poured into a separatory funnel. The product layer was removed and washed a second time with 1000 mL of fresh distilled water. The product layer was stripped under aspirator vacuum on a steam pot until most of the dichloromethane had been removed. While still hot, with vigorous stirring 2500-3000 mL of heptane was added, then cooled to 20°-25° C. and stirred 1-2 hours. The greenish white product was collected, washed with heptane and dried in a warm air oven overnight. The yield of green-white crystals was 467.9 g (74%): MP 97°-99° C.; IR (KBr) (>C=N) 6.33$\mu$, (N→O) 8.65$\mu$; NMR (CCl$_4$, Me$_4$Si) $\delta$1.3 (T, 3H), 2.4 (S, 3H), 2.7 (Q, 2H), 7.2 (D, 4H), 7.7 (Q, 2H), 7.8 (S, 1H), 8.2 (D, 2H); TLC (1 BuOAc, 2 PhCH$_3$, 4 CHCl$_3$, 4 CHCl$_3$), silica-gel coated plates, viewed under short-wave UV light, major spot for the desired nitrone, Rf=0.50.

EXAMPLE 2

2-(2',4'-Di-tert-pentylphenoxy)-4'''-(N-benzylideneamineoxide)hexananilide

In a 2000-mL, 3-necked round bottom flask equipped with a stirrer, thermometer and 20°-25° C. water bath was placed 160 g (0.342 moles, 1.0 equiv.) of 2-(2'4'-di-tert-pentylphenoxy)-4'''-nitrohexananilide and 1400 mL of methanol. This was heated to $\simeq$50° C. to dissolve and then cooled to 20°-25° C. Zinc dust (44.8 g–0.685 moles, 4.0 equiv.), 47.0 g (0.443 moles, 1.3 equiv.) of benzaldehyde, and 5-6 mL of water was then added. The water was added to start the reaction and also prevent or shorten the induction period. Then dropwise 102.6 g (1.708 moles, 5.0 equiv.) of acetic acid was added over a 15 minute period. The reaction exotherm temperature was held below 45° C. with the water bath. When the acetic acid addition was complete, the water bath was removed and the reaction temperature was allowed to drift down to room temperature. The reaction mixture turned lime green. About 1 hour after the acetic acid addition was complete, the reaction mixture formed a thick greenish-white precipitate, which signifies reaction completion. The TLC (1 BuOAc, 2 PhCH$_3$, 4 CHCl$_3$) showed reaction completion. Dichloromethane (750 mL) was added to the reaction mixture to dissolve the precipitated product. The zinc acetate salts were filtered off and the liquors were stripped to a mush. The mush was dissolved in 800 mL of dichloromethane and mor salts were filtered. The liquors were given an 800-mL water wash, stripped to an oil, and the product oil crystallized from 1000 mL of heptane. The greenish-white crystals were collected, washed with 100 mL of heptane and dried in a warm vacuum oven. The yield of fluffy crystals was 136.4 g (73.5%): MP 132°–135° C.; IR (KBr)>C=N (6.25μ), (N→O) 8.30μ; NMR (acetone-D$_6$, Me$_4$Si), δ0.7 (M, 7H), 1.2 (S, 6H), 1.5 (M, 12H), 2.1 (M, 6H), 4.85 (T, 1H), 6.85 (D, 1H), 7.13 (Q, 1H), 7.5 (T, 3H), 7.9 (Q, 4H), 8.4 (S, 1H), 8.6 (Q, 2H), 9.3 (S, 1H); TLC (1 BuOAc, 2 PhCH$_3$, 4 CHCl$_3$), silica-gel-coated plates, viewed under short-wave UV light, major spot R$_f$=0.57.

EXAMPLE 3

2-Amino-5-ethylphenol hydrochloride

In a 500-mL 3-necked round bottom flask equipped with a stirrer, thermometer, and 15°–20° C. water bath was placed 40 g (0.264 moles, 1.0 equiv.) of 4-ethylnitrobenzene, 230 mL of methanol, 30 mL of water, 30.8 g (0.2904 moles, 1.1 equiv.) of benzaldehyde, and 36.6 g (0.561 moles, 4.25 equiv.) of zinc powder. The reaction mixture, with vigorous stirring, was cooled to 15°–20° C. and the dropwise addition of 79.2 (1.32 moles, 5.0 equiv.) of acetic acid was begun. The reaction mixture was allowed to exotherm to 34°–36° C., and the temperature was held there throughout the 30 minute addition period. When the addition was complete, the reaction temperature was held at 35° C. with a steam pot for 1 hour. The reaction flask was placed under full aspirator vacuum and the reaction mixture was stripped to about ⅓ volume. Xylene (100 mL) was added to the reaction mixture to azeotrope water from the reaction mixture. This azeotrope step was repeated 2 more times with fresh xylene. The zinc acetate salts were filtered off. The xylene/product liquors were stripped to an oil under aspirator vacuum. Dichloromethane (250 mL) was added to the product oil and cooled to 0° C. Via an addition funnel, 49.6 g (0.273 moles, 1.033 equiv.) of trichloroacetyl chloride was added maintaining the reaction temperature below 20° C. The resulting dark solution was warmed to 25° C. and held here for 15 minutes to form a compound of this invention having Formula (I). Acetic acid (44 mL) was added in one portion, followed by 27 g (0.32 moles, 1 equiv.) of concentrated hydrochloric acid. The reaction mixture was heated, and the low boiling liquid (lower than 50° C.) was distilled off. When the pot temperature reached 78°–80° C. and no more volatile liquids distilled, the reaction was allowed to reflux for 3 hours (at 78°–85° C.). The reaction was cooled to 50° C. and 600 mL of ethyl acetate was added in one portion. The dark solution was stirred and cooled to 15°–20° C. The 2-amino-5-ethylphenol hydrochloride came out of solution slowly. The mixture was stirred at 15°–20° C. for 30 minutes then collected and washed with ethyl acetate and heptane. The fluffy yellow-orange crystals were dried in a warm air oven overnight. The 24.4 g yield of 15 was 53.2% of the theoretical: MP 218° C.±2° C.; HPLC (area %) 78.0%; IR (KBr)$^{16}$(OH) 3.0μ and 7.0μ, (—NH$_2$.HCl) 3.9μ and 5.25μ; NMR (DMSO-D$_6$, Me$_4$Si) δ1.1 (t,3H), 2.5 (q,2H), 6.65 (d, 1H), 6.9 (S, 1H), 7.3 (T, 2H), 10 (S, 2H), 10.7 (S, 1H); TLC (1 BuOAc, 2 PhCH$_3$, 4 CHCl$_3$), silica-gel-coated plates, viewed under short-wave UV light, major spot for 15, R$_f$=0.18.

EXAMPLE 4

Under a nitrogen atmosphere a 22-L., four neck vacuum setup, was charged with 2.7 Kg. (12 moles) of N-benzylidene-4-ethylbenzene-amine N-oxide and 12 L. of THF. With stirring, solution occurred at room temperature in 10–15 minutes and the dark solution was cooled to −6° C. with an ice/acetone bath. Over a period of 2 hours, while holding the temperature at 0° to 10° C., 2.25 Kg./1390 mL. (12.4 moles) of trichloroacetyl chloride was added slowly. The reaction was very exothermic during the addition of the first liter of trichloroacetyl chloride and a yellow precipitate formed immediately. Shortly after the addition was complete, the intermediate crystallized out massively. The stirrer was not stopped by the large mass of soft crystals and the mass slowly broke up with continued stirring. The reaction was warmed to 25° C. and held there for 1 hour. At this point the whole reaction was stirring well and 3 L. (34.8 moles) of concentrated HCl, were added slowly bringing about complete solution and a slow exotherm to 40° C. The reaction was then heated to reflux at 75° C. overnight.

In the morning the THF was stripped off over a 2.5 hour period, with aspirator vacuum to a pot temperature of 70° C. The concentrate was about 7 L. which was cooled to 45° C.; where 13 L. of ethyl acetate were added. Cooling was continued and at 35° C. a massive crystallization occurred again. Once broken up, cooling with stirring was continued to 13° C. The light yellow product was collected, washed with 2 L. of ethyl acetate, and dried in an air oven. This yielded 1245 g. (60%) of 2-amino-5-ethylphenol hydrochloride.

| Analytical: | |
|---|---|
| Appearance: | Peach colored fluffy solid |
| M.P.: | 230–231° C. |
| IR: | Consistent with the assigned structure |
| NMR: | Consistent with the assigned structure |
| TGA: | 0.1% loss |
| DSC: | No melt, transition at 161.5° C. |
| LC: | 94.1% |
| Titration: | TMAH-88.9% |
| | HClO$_4$-0.03% free amine |
| | AgNO$_3$-91.5% |

Following the above procedures, compounds of Formula (I) can be prepared by reacting a trihaloacetyl halide with a nitrone, as discussed in detail in this Specification. Thus, results similar to those illustrated in the preceeding example can be achieved by reacting a nitrone with an acyl halide as described above at a temperature in the range of 0°–50° C., for a time of 0.5–60 minutes to form a compound of Formula (I) and then hydrolyzing at a temperature in the same for about the same time.

This invention has been described in particular reference to preferred embodiments.

A skilled practitioner, familiar with the above detailed description, can make many modifications and substitutions without departing from the scope and spirit of the following claims.

We claim:

1. A process for formation of a compound having the formula:

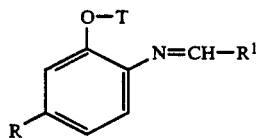

wherein T has the formula:

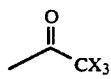

wherein each X is independently selected from the group consisting of chlorine, bromine, and iodine, R is an alkyl group having 1 to 30 carbon atoms or a coupling off group, and R' is an alkyl or aryl group having 1 to 10 carbon atoms;

said process comprising reacting an acid halide which is a trihaloacetyl halide, with a nitrone having the formula:

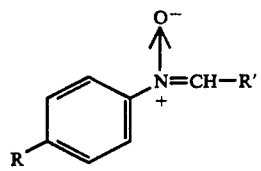

wherein R and R' are defined above at a temperature of from about $-10°$ C. to $80°$ C. and under substantially anhydrous conditions.

2. Process of claim 1 wherein it is conducted in an inert solvent.

3. Process of claim 1 wherein said acid halide is trichloroacetyl chloride.

4. Process of claim 3 wherein said nitrone is

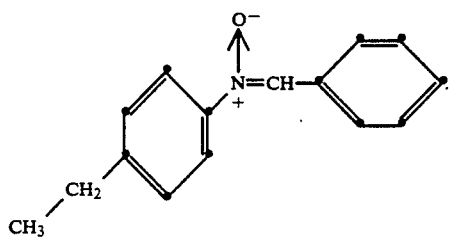

* * * * *

UNITED STATES PATENT AND TRADEMARK OFFICE
CERTIFICATE OF CORRECTION

PATENT NO. : 5,214,194
DATED : May 25, 1993
INVENTOR(S) : Tang, et al.

It is certified that error appears in the above-indentified patent and that said Letters Patent is hereby corrected as shown below:

Column 11, line 5, in the formula "$R^1$" should be --$R'$--.

Signed and Sealed this

First Day of February, 1994

Attest:

BRUCE LEHMAN

Attesting Officer

Commissioner of Patents and Trademarks